United States Patent [19]

Demers

[11] Patent Number: 4,864,032

[45] Date of Patent: Sep. 5, 1989

[54] PROCESS FOR THE PREPARATION OF INDAZOLES

[75] Inventor: James P. Demers, New York, N.Y.

[73] Assignee: Ortho Pharmaceutical Corporation

[21] Appl. No.: 69,073

[22] Filed: Jul. 2, 1987

[51] Int. Cl.$^4$ ............................................. C07D 231/56
[52] U.S. Cl. .................................... 548/359; 548/238; 548/372; 564/310; 564/314
[58] Field of Search .................... 548/359, 372, 238; 564/310, 314

[56] References Cited

PUBLICATIONS

Wiley, Pyrazoles, Pyrazolines, Pyrazolidines, Indazoles and Condensed Rings, (1967) p. 289.

*Primary Examiner*—Robert W. Ramsuer

[57] ABSTRACT

A process for the preparation of aryl hydrazines and indazoles by reacting organometallic regents with azodicarboxylates.

3 Claims, No Drawings

PROCESS FOR THE PREPARATION OF INDAZOLES

BACKGROUND OF THE INVENTION

1. Field of the Invention

The present invention relates to a novel process for the preparation of aryl hydrazines of the following formula:

and indazoles of the following formula:

as described further below. Aryl hydrazines and indazoles are useful pharmacological intermediates.

2. Description of the Prior Art

Aryl hydrazines are useful as intermediates for dyes, agricultural chemicals and pharmaceuticals. Indazoles are useful as pharmaceuticals, dyes and photographic coupling agents.

Currently known methods for preparing aryl hydrazines involve reducing the corresponding diazonium salts with sulfite or other reducing agents (Coleman, G., *Org. Syn. Coll.* Vol. I, 442 (1941)), or by electrolysis (Takayanagi, *J. Chem. Soc. Japan* 53, 427 (1932)). The former method is not generally applicable to substituted hydrazines, and requires careful attention to reaction conditions. The latter method requires specialized apparatus. Other methods involve N-animation of anilines, which require specialized reagents (Ohme, R. et al., in *Preparative Organic Chemistry*, Hilgetag et al., Eds., John Wiley & Sons, New York, p. 586 (1972)), and rearrangements of N-halo ureas (Murakami, Y., *Chem. Pharm. Bull.* 31, 423 (1983)). All of these methods require that the corresponding aniline be available.

The prior art reveals that Grignard reagents have been added to the N=N double bonds of diazirenes (*Angewandte Chemie* 73, 220 (1961)) and diazoalkanes (*J. Org. Chem.* 23, 1595 (1958)). Additionally, tert-butyl magnesium chloride has been added to di-t-butylazodicarboxylate, and the product converted to t-butylhydrazine (*J. Org. Chem.* 26, 4336 (1961)). The addition of enolates to azodicarboxylates has also been reported by J. C. Vederas at the International Symposium on the Chemistry of Natural Products, Edmonton, Alberta, Canada, June 25, 1985.

SUMMARY OF THE INVENTION

The present invention is directed to a process for preparing aryl hydrazines and to a process for preparing indazoles. The process is shown in Scheme I:

SCHEME I where
- M may be Li or MgX;
- X may be Cl, Br or I;
- R may be one or more of Cl, F, $N(R_4)_2$, $OR_4$, $R_4$, $SR_4$ and 4,4-dimethyl-2-oxazolinyl, or together with the phenyl ring may form a fused aromatic ring system such as a naphthalene ring system;
- $R_1$ may be H, F, 4,4-dimethyl-2-oxazolinyl, F, $N(R_4)_2$, $OR_4$, $R_4$ and $SR_4$, or $R_1$ may be a fused aromatic ring system such as a naphthalene ring system;
- $R_2$ may be alkyl, aralkyl, haloalkyl or any other protecting group compatible with the organometallic reagent 1, especially benzyl, t-butyl and 2,2,2-trichloroethyl;
- $R_3$ may be OH, $-OCH_2C(CH_3)_2NH_2$ or $-NHC(CH_3)_2CH_2OH$, and
- $R_4$ may be $C_1$-$C_6$ alkyl optionally substituted with one or more of F, or aryl.

The present invention also encompasses the novel compound 4-(2,2,2-trifluoroethoxy)phenylhydrazine.

Advantages of the present method for preparing aryl hydrazines are that no specialized apparatus or specialized reagents are needed, as is the case with some prior art processes. Additionally, the present method is applicable to substituted hydrazines, which is not true of some of the prior art methods. All of the prior art processes start with the aniline compound. In the present method, the availability of the corresponding aniline is not required.

DETAILED DESCRIPTION OF THE INVENTION

The invention in its broadest aspects relates to a process for preparing aryl hydrazines and heterocycles derived from aryl hydrazines. The invention also encompass a process for preparing indazoles. Aryl hydrazines and indazoles ae useful as intermediates for dyes, agircultural chemicals and pharmaceuticals.

The process fir preparing the aryl hydrazines and indazoles according to the invention is shown in Scheme I above.

The reaction between the organometallic reagent 1 and the azodicarboxylate 2 is performed in an inert solvent such as tetrahydrofuran at a relatively low temperature between about −75° C. and 0° C. under an inert atmosphere such as nitrogen gas. The product 3 is obtained by acid hydrolysis of the reaction mixture. Acetic acid is most commonly used for the acid hydrolysis. The protecting group $R_2$ is removed by known methods approximate to the nature of $R_2$ to provide the aryl hydrazines 4 or indazoles 5. When the protecting group $R_2$ is an ethyl group, the most common method for its removal is to dissolve the material 3 in isopropanol to which potassium hydroxide is added. The mixture is then refluxed under nitrogen, and neutralized with acetic acid. After the mixture is evaporated, the residue is treated with ether and aqueous sodium hydroxide.

When the protecting group $R_2$ is a t-butyl group, a common method for its removal is to dissolve the material 3 in isopropanol and pass hydrogen chloride gas through the solution. After the solution is evaporated, the residue is treated with ether and the solids collected by filtration.

The following examples describe the invention in greater particularly and are intended to be a way of illustrating but not limiting the invention.

EXAMPLE 1

3,4-Dimethoxyphenylhydrazine

A solution of 3,4-dimethoxyphenylmagnesium bromide (prepared from 10.85 g, 50 mmol of 3,4-dimethoxybromobenzene and 1.34 g, 55 mmol magnesium) in 200 ml tetrahydrofuran (hereinafter THF) was cooled to −75° C. and added to a solution of diethyl azodicarboxylate (8.71 g, 50 mmol) in 250 ml THF at −75° C. under an inert atmosphere. The solution was allowed to warm to 0° C. and acetic acid (3 g, 50 mmol) and $H_2O$ (20 ml) were added. The organic solution was dried over $MgSO_4$, filtered and evaporated, providing N,N'-bis(ethoxycarbonyl)-3,4-dimethoxyphenylhydrazine as a red oil (15 g, 96% yield). This material was dissolved in isopropanol (500 ml) and 15 g potassium hydroxide was added. The mixture was refluxed under nitrogen for four hours, cooled, and neutralized with acetic acid (15 ml). The mixture was evaporated, the residue was treated with ether and aqueous sodium hydroxide, and the ether solution was dried over $MgSO_4$, filtered and distilled in vacuo. Veratrole was distilled from the mixture, followed by 3,4-dimethoxyphenylhydrazine, which was crystallized from carbon tetrachloride to provide 1.0 g off-white powder, mp 103°–106° C. (dec).

EXAMPLE 2

4-Methylthiophenylhydrazine

4-Bromothioanisole (10.0 g, 49.2 mmol) and magnesium turnings (1.5 g, 62 mmol) were refluxed for one hour under nitrogen in 100 ml THF. The resulting solution of 4-(methylthio)phenylmagnesium bromide was cooled to −75° C. and added to a solution of di-t-butylazodicarboxylate (11.3 g, 49 mmol) in 150 ml THF at −75° C. under a nitrogen atmosphere. After 10 minutes, acetic acid (3 ml, 50 mmol) was added and the mixture was allowed to warm to room temperature. Water (30 ml) and ether (100 ml) were added, and the organic layer was washed with saturated aqueous sodium chloride, dried over $MgSO_4$, filtered and evaporated, leaving N,N'-bis(t-butoxycarbonyl)-4-methylthiophenylhydrazine as a yellow oil. This material was dissolved in isopropanol (500 ml), and a solution of hydrogen chloride (4.8M) in dioxane (100 ml) was added. The mixture was refluxed for 15 minutes, cooled, and diluted with 250 ml ether. The resulting precipitate was collected by filtration and dried in vacuo, providing 7.0 g 4-methylthiophenylhydrazine hydrochloride as a beige solid, mp 198°–199° C. (dec) (75% overall yield).

EXAMPLE 3

Phenylhydrazine Hydrochloride

A solution of 1.95M phenyllithium in cyclohexane-ether (10.3 ml, 20 mmol) was added slowly to a stirred solution of di-t-butylazodicarboxylate (4.6 g, 20 mmol) in THF at −75° C. under a nitrogen atmosphere. The solution was allowed to warm to −40° C., and acetic acid (1.5 ml, 25 mmol) and water (5 ml) were added. The mixture was allowed to warm to 0° C., and the organic layer was decanted, dried over $MgSO_4$, and evaporated. The residue was crystallized from hexane, and provided N,N'-bis(t-butoxycarbonyl)phenylhydrazine as a white powder (3.7 g, 60% yield). This material was dissolved in 50 ml isopropanol, and hydrogen chloride gas was passed into the solution until it became hot. After 30 minutes, the solution was diluted with 100 ml ether, and the precipitate collected by filtration. The filtrate was concentrated to dryness, and the residue treated with ether to provide a second crop. A total of 1.5 g (88% yield) phenylhydrazine hydrochloride, mp 248°–250° C. (dec) was obtained as white flakes.

EXAMPLE 4

2-(Trifluoromethyl)phenylhydrazine

2-Bromobenzotrifluoride (4.5 g, 20 mmol) and magnesium turnings (0.54 g, 22 mmol) were refluxed under a nitrogen atmosphere in 100 ml THF until the magnesium had dissolved. The resulting solution was cooled to −75° C. and added to 4.6 g (20 mmol) di-t-butyl azodicarboxylate in 100 ml THF at −75° C. The solution was warmed to −40° C., acetic acid (1.5 ml, 25 mmol) was added, and the mixture concentrated to 20 ml. Hexane and water were added, and the hexane solution was evaporated to leave a brown oil which was chromatographed on silica with 10% ether in $CHCl_3$, providing 6.1 g (81% yield) of N,N'-bis(t-butoxycarbonyl)-2-(trifluoromethyl)phenylhydrazine as a brown gum. This material was dissolved in 200 ml isopropanol, and hydrogen chloride gas was passed into the solution resulting in a weight gain of 8 g. The solution was stirred at 50° C. for 30 minutes, then evaporated to dryness. The residue was treated with ether, and the solids collected by filtration and dried in vacuo, providing 2.7 g (79% yield) 2-(trifluoromethyl)phenylhydrazine hydrochloride as a white powder, mp 241°–242° C.

EXAMPLE 5

6-Methoxy-2-naphthylhydrazine hydrochloride

2-Bromo-6-methoxy naphthalene (4.75 g, 20 mmol) was converted to a Grignard reagent, and reacted with di-t-butylazodicarboxylate (4.5 g, 19 mmol), as in Example 4 above. A similar work-up, and chromatography on silica with 5% ether in 1,2-dichloroethane, provided 3.5 g (47% yield) N,N'-bis(t-butoxycarbonyl)-6-methoxy-2-naphthylhydrazine as a brown gum. This was converted with hydrogen chloride in isopropanol, by the method in Example 4, to 6-methoxy-2-naphthylhydrazine hydrochloride (1.35 g, 67% yield) as an off-white powder, mp 207°–208° C. (dec).

EXAMPLE 6

4-Pentoxyphenylhydrazine hydrochloride

By the method of Example 4 above, 4-bromophenyl pentyl ether (4.86 g, 20 mmol) was converted to 4-pentoxyphenylhydrazine hydrochloride, mp 177°–178° C. (dec) in an overall yield of 60%.

EXAMPLE 7

4-(2,2,2-Trifluoroethoxy)phenylhydrazine hydrochloride

A solution of 4-bromophenyl 2,2,2-trifluoroethyl ether (5.2 g, 20 mmol) in THF (75 ml) was cooled to −75° C. under nitrogen. A solution of 2.7M n-butyllithium (7.5 ml, 20 mmol) was added dropwise. After 15 minutes, a solution of di-t-butylazodicarboxylate (4.5 g, 19 mmol) in THF (30 ml) was added quickly with stirring. The solution was allowed to warm to −40° C., resulting in the formation of a precipitate. Acetic acid (1.5 ml), water (10 ml), saturated sodium chloride (10 ml) and hexane (100 ml) were then added to the mixture. The organic solution was dried over MgSO$_4$, filtered and evaporated. The residue was dissolved in 1:1 carbon tetrachloride-hexane and left to crystallize overnight. The resulting crystalline precipitate was collected, providing 4.25 g of white powder. A second crop (from 1:2 carbon tetrachloridehexane) provided a total of 4.95 g (61% yield) N,N'-bis(t-butoxycarbonyl)-4-(2,2,2-trifluoroethoxy)phenylhydrazine, mp 140°–141° C. This was converted, by treatment with 500 ml of 2.5% HCl in isopropanol for 16 hours at 20° C., to 4-(2,2,2-trifluoroethoxy)phenylhydrazine hydrochloride (43% yield), mp 185°–186° C. (dec).

EXAMPLE 8

3-Hydroxy-6,7-dimethoxy-1H-indazole

A solution of 2-(3,4-dimethoxyphenyl)-4,4-dimethyloxazoline (23.5 g, 0.10 mol) in 500 ml THF was cooled to −60° C., and n-butyllithium (37 ml of 2.7M hexane solution) was added slowly with stirring under nitrogen. After 30 minutes, the solution was cooled to −75° C. and a solution of di-t-butylazodicarboxylate (23.0 g, 0.10 mol) in 100 ml THF was quickly added. The mixture was warmed to −20° C., and acetic acid (6.5 ml) and water (10 ml) were added. The organic solution was decanted, evaporated and chromatographed on silica with 10% ether in CH$_2$Cl$_2$, providing 42 g (90% yield) N,N'-bis(t-butoxycarbonyl)-2,3-dimethoxy-6-(4,4-dimethyl-2-oxazolinyl)phenylhydrazine, as an amorphous tan solid. A solution of this material (36 g) in 1000 ml ethyl acetate was cooled to 10° C., and hydrogen chloride gas was passed in, with cooling, until no further precipitation was observed. The mixture was allowed to stand for two days, and the precipitate was collected by filtration and dissolved in 200 ml water. The pH was adjusted to 11 with sodium hydroxide, and the mixture extracted with dichloroethane. The organic solution was concentrated and chromatographed on silica with 10% isopropanol and 5% triethylamine in t-butyl methyl ether, providing 1.3 g (6.3% yield) of 6,7-dimethoxy-3-(1,1-dimethyl-2-hydroxyethylamino)-1H-indazole, mp 118°–119° C., and 8.7 g (42% yield) of 3-(2-amino-2-methylpropoxy)-6,7-dimethoxy-1H-indazole as a brown oil, mp of hemisulfate hemihydrate 226°–227° C. (from H$_2$O-isopropanol). The alkaline, aqueous solution remaining from the extraction was adjusted to pH 8.0 with hydrochloric acid, and the resulting precipitate collected by filtration and recrystallized from isopropanol-t-butyl methyl ether to provide 1.7 g (11% yield) of 3-hydroxy-6,7-dimethoxy-1H-indazole, mp 175° C. with rapid heating, 185°–187° C. with slow heating.

What is claimed is:

1. A process for the preparation of indazoles comprising (a) reacting an organometallic reagent of the formula

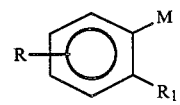

wherein

M is Li or MgX,

X is Cl, Br or I,

R is one or more of Cl, F, N(R$_4$)$_2$, OR$_4$, R$_4$, SR$_4$, and 4,4-dimethyl-2-oxazolinyl, or together with the phenyl ring is a fused aromatic ring system, R$_1$ is 4,4-dimethyl-2-oxazolinyl, R$_4$ is C$_1$–C$_6$ alkyl, C$_1$–C$_6$ alkyl substituted with F, or aryl, with an azodicarboxylate of the formula

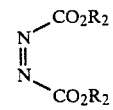

wherein R$_2$ is alkyl, aralkyl, haloalkyl or other protecting group compatible with the organometallic reagent, to yield an intermediate compound of the formula

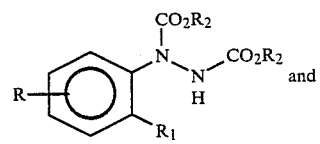 and (b) removing the protecting group R$_2$ from the intermediate compound to yield an indazole of the formula

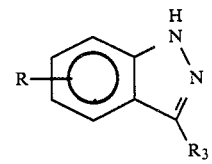

where R$_3$ is OH, −OCH$_2$C(CH$_3$)$_2$NH$_2$ or −NHC(CH$_3$)$_2$CH$_2$OH.

2. The process of claim 1 wherein said protecting group R$_2$ is benzyl, t-butyl or 2,2,2-trichloroethyl.

3. The process of claim 1 wherein said protecting group R$_2$ is an ethyl group and is removed from said intermediate compound by dissolving the intermediate compound in isopropanol to which potassium hydroxide has been added.